United States Patent [19]
Aqui et al.

[11] Patent Number: 5,347,138
[45] Date of Patent: Sep. 13, 1994

[54] IN SITU REAL TIME PARTICLE MONITOR FOR A SPUTTER COATER CHAMBER

[75] Inventors: Derek G. Aqui, San Jose; Peter G. Borden, San Mateo, both of Calif.

[73] Assignee: High Yield Technology, Sunnyvale, Calif.

[21] Appl. No.: 41,088

[22] Filed: Apr. 1, 1993

[51] Int. Cl.⁵ ............................................. G01N 15/06
[52] U.S. Cl. ................................... 250/573; 356/343
[58] Field of Search ...................... 250/573, 574, 575; 356/335, 343, 37, 338

[56] References Cited

U.S. PATENT DOCUMENTS

| | | | |
|---|---|---|---|
| 4,707,133 | 11/1987 | Roberts et al. | 356/230 |
| 5,061,070 | 10/1991 | Batchelder et al. | 356/345 |

Primary Examiner—David C. Nelms
Attorney, Agent, or Firm—Skjerven, Morrill, MacPherson, Franklin & Friel

[57] ABSTRACT

A structure and a method use a non-invasive particle monitor to detect particles in a process chamber for a "down sputtering" metal deposition process. In one embodiment, only non-spherical particles are detected using a single laser beam of a predetermined polarization is used, and the phase shift in the polarization due to the passing of a particle through the laser beam is measured. In another embodiment, two closely spaced orthogonally polarized laser beams are used, and the differential intensity of the laser beams is measured when a particle passes through one of the laser beams. In another embodiment, shield tubes for housing optical components are used to prevent coating of the optical components and to prevent deposition to take place outside the shielded area. Internal electric and magnetic fields are used to drive particles through the laser beams for particle detection.

18 Claims, 4 Drawing Sheets

IN SITU REAL TIME PARTICLE MONITOR FOR A SPUTTER COATER CHAMBER

BACKGROUND OF THE INVENTION

1. Field of the Invention

The present invention relates to non-invasive particle monitors. In particular, the present invention relates to "bright field" particle monitors, which detect particles by monitoring a change in the intensity and/or phase in an incident laser beam.

2. Discussion of the Related Art

In the metal deposition step used in the manufacturing of integrated circuits, avoidance of contamination is critical. Metal deposition is typically accomplished by a sputtering process, in which a metal target is bombarded with ions of a plasma contained in a low pressure process chamber. In one such sputtering process, the cathode is used as a metal target for a low pressure argon plasma created between the cathode and the anode. The argon ions in the plasma dislodge from the cathode metal atoms (e.g. aluminum), which drift to a semiconductor wafer placed in the process chamber, thereby creating on the exposed surface of the semiconductor wafer a coating of the metal. Inherently, a metal deposition process is associated with a high particle level because metal coating occurs not only on the semiconductor wafer, but also in the process chamber, and the instrumentation installed in the process chamber. As the metal coating in the process chamber accumulates over time, particles of the coating can flake off to contaminate the semiconductor wafer being processed in the process chamber. Such contamination is a critical problem affecting manufacturing cost, because metal deposition typically is one of the final steps in a manufacturing process, when the semiconductor wafer has the greatest value.

Conventional particle monitoring techniques employ laser light scattering sensors, such as those disclosed in U.S. Pat. No. 4,739,177 to Peter Borden, entitled "Particle Detector for Wafer Processing Equipment" filed on Sep. 16, 1986, and issued on Jun. 19, 1988. In a conventional light scattering sensor, a detector, such as a silicon photodiode, detects light scattered from particles passing through an intense laser beam. Such a method for detecting particles has been employed to monitor particles in a production sputter coater, which is configured such that the semiconductor wafer and the cathode are oriented vertically (called "side sputtering"). In this configuration, the detector is placed beneath the sputtering area, so as to capture light scattered by particles falling through a laser beam located outside the region where sputtering occurs.

However, many of the more recent sputtering systems use a configuration called "down sputtering." In this configuration, the cathode, also acting as the metal target, is mounted above the semiconductor wafer. Because gas pressure in the process chamber is relatively low—typically 0.01 Torr—there is too little gas present to carry particles away from the sputtering region. The particles are contained in the plasma by electrostatic forces and are thus unseen by a particle monitor located outside the region in which metal deposition occurs. Thus, conventional techniques described above cannot be used in a down sputtering process chamber.

For a "down sputtering" system, a desired particle monitor preferably detects particles that are close to and above the exposed surface of the semiconductor wafer. Necessarily, such a particle monitor should be capable of detecting the minute amount of light scattered from the laser beam, while filtering out the light or "glow" from the plasma. Further, the particle monitor's optics should preferably be protected from metal deposition, and the presence of the particle monitor should have little effect on the metal deposition process.

One practical method is bright field differential detection. In a bright field differential detector (hereinafter "differential detector"), two closely spaced, nearly overlapping, laser beams are projected in the space above the semiconductor wafer. When a particle passes through one of the laser beams, the light scattered from the laser beam causes a phase shift relative to the other beam. This phase shift can be very accurately measured. In fact, such a technique has been used to detect particles as small as 0.03 $\mu$m diameter in liquids and in silicon—the smallest particles detected by any optical technique.

There are a number of advantages in using the bright field differential detection technique. First, because the measurement is based on a difference between two nearly overlapping beams, the measurement is virtually insensitive to common mode noise caused by mechanical vibrations, electrical noise, or optical noise. This differential technique is also insensitive to imperfections in the windows or the intermediate optical surfaces the laser beams pass through. Second, a differential detector is insensitive to optical noises, such as the plasma glow or background light, whose contribution to the measurement is averaged out. Third, since a bright field detector requires only a very small view aperture for the laser beams to pass, the portion of plasma glow seen by the detector is minimized such that the effect of noise from plasma glow is also minimized. Fourth, as a bright field technique (i.e. the measurement is made directly from the incident laser beams), the laser beams can be projected over a long distance to maximize the region of particle detection, and to allow the source of the laser beams and the photodetectors to be placed outside the process chamber. In a bright field detector, only the infrared laser beams pass through the vacuum itself. Finally, even with all the sophistication of the differential detection techniques, the optics required are relatively simple and all components are readily available, such that the resulting system is relatively robust.

One light scattering particle detector that meets many of the above requirements is disclosed, in a copending U.S. patent application by Peter Borden, Ser. No. 07/824,619, entitled "A non-invasive Particle Monitor for sealed HDAs," filed on Jan. 23 1992, and assigned to High Yield Technology, which is also the Assignee of the present invention. In this copending U.S. Patent Application, which is hereby incorporated by reference in its entirety, is disclosed a sensor which passes a laser beam through a region where particles are to be detected and uses a differential polarization technique to provide noise immunity and increased sensitivity.

Another example of a non-invasive sensor is described in U.S. Pat. No. 5,037,202, to Batchelder et al, entitled "Measurement of size and Refractive Index of Particles Using Forward-scattered Electromagnetic fields." Batchelder's sensor measures the sizes and refractive indices of particles in a fluid using the relative phase shift and intensity of two closely spaced, orthogonally polarized, laser beams. However, Batchelder et al requires the use of a circularly polarized laser beam. To achieve the phase shift in Batchelder et al, it is required that the closely spaced laser beams recombine to cause the necessary beam interference. The system of Batchelder et al does not work with linearly polarized laser beams.

SUMMARY OF THE INVENTION

In accordance with the present invention, a method and a structure are disclosed for providing, in a down sputter process chamber, particle detection using a bright field detector over a wide area above a semiconductor wafer.

In accordance with one aspect of the present invention, the laser beam is provided an oval cross section, with its major axis aligned substantially vertically to increase the area in which particle detection can take place.

In accordance with another aspect of the present invention, long and narrow shield tubes each having a length of no less than three mean free paths of the gas molecules in the process chamber and a width less than one mean free path of the gas molecules in the process chamber are used to prevent metal deposition on the optical components of the system and to prevent deposition outside the shielded area of the process chamber through the openings introduced by installation of the particle monitor.

In accordance with another aspect of the present invention, the shield tubes open to the process chamber at a cross section of a larger size and tapering, for most of the length of the shield tube, to a cross section close to the cross section of the laser beam, so as to accommodate deposition at its opening to the process chamber.

In accordance with another aspect of the present invention, internal electric and magnetic fields are used to drive particles through the laser beam, thereby allowing the use of small cross section stationary laser beams, and allowing placements of entry and exit points of the laser beams to easy access portions of the process chamber.

The present invention has numerous advantages over in situ and surface particle monitoring techniques presently available. First, the particle monitor of the present invention can be used in a sputtering process where the pressure is too low to carry particles away from the region of the metal deposition.

Second, the particle monitor of the present invention measures the particle level directly above the semiconductor wafer, including particles which are suspended in the plasma by electrostatic forces. In this manner, the particle monitor of the present invention detects particles unlikely to be seen by detectors located outside of the region directly above the wafer. By monitoring the particle level directly above the semiconductor wafer, the particle monitor of the present invention increases the likelihood that the measured particle level correlates directly with wafer contamination.

Third, the particle monitor of the present invention provides a real-time measurement of the particle level during processing of a semiconductor wafer, thereby providing a figure of merit for process control and diagnostics under the conditions actually seen by the product.

The present invention is better understood upon consideration of the detailed description below and the accompanying drawings.

DETAILED DESCRIPTION OF THE PREFERRED EMBODIMENTS

Figure 1:
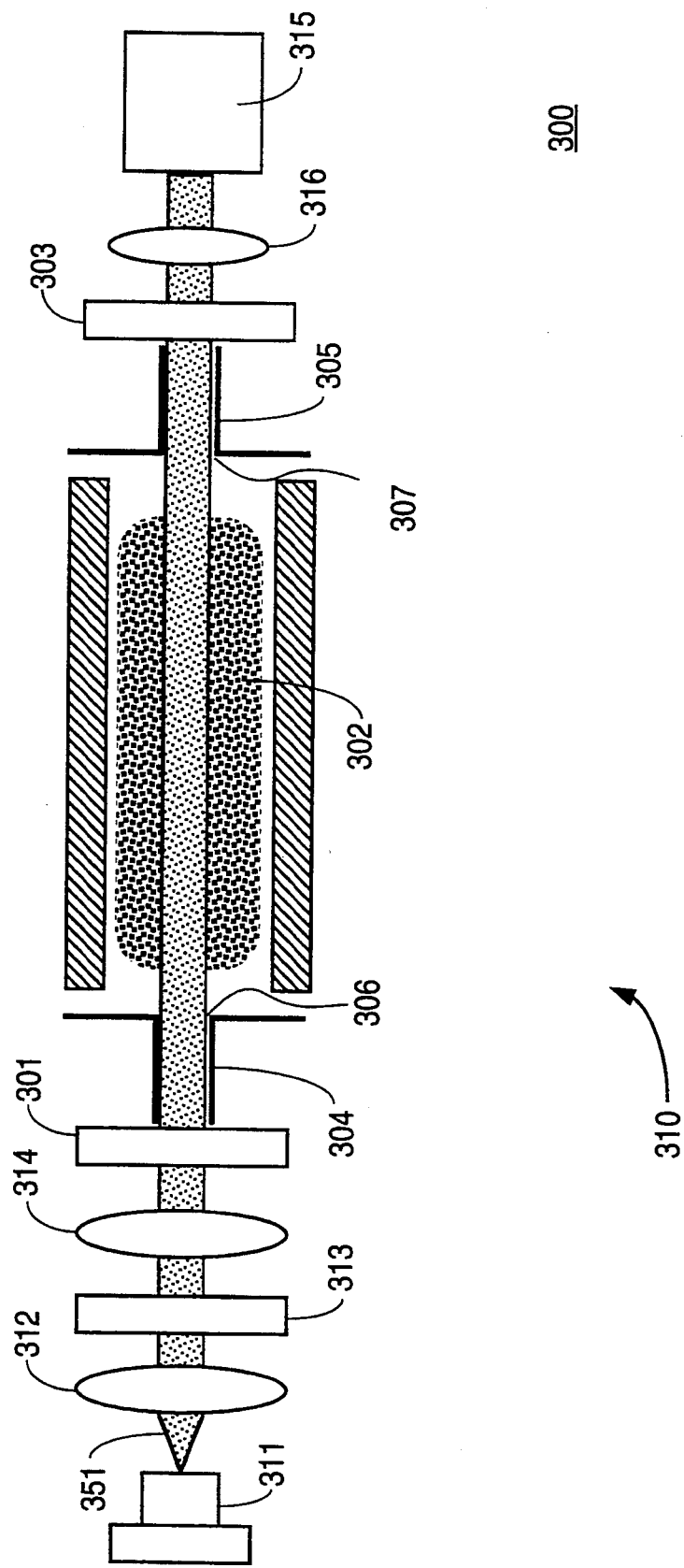
FIG. 1 shows a particle monitor 310 installed for measuring the particle level in sputtering chamber 300.

One embodiment of the present invention, based on a bright field sensor is shown as particle monitor 310 in FIG. 1. Particle monitor 310 uses a single laser beam to detect non-spherical particles.[1] A non-spherical particle scatters light preferentially in one direction of (linear) polarization. A non-spherical particle passing through a laser beam would reduce the intensity of the laser beam in the direction of the preferred polarization, to result in a measurable phase shift in polarization in the resulting laser beam. Thus, unlike spherical particles, non-spherical particles can be detected by placing a beam splitter oriented 45 degrees to the polarization of the pg,9 incident beam, and then measuring the relative intensity between the orthogonally polarized laser beams emerging from the beam splitter. Therefore, the detection of non-spherical particles can be accomplished using only a single laser beam. Using one single laser beam simplifies the optics of the particle monitor without imposing a significant limitation to particle monitor 310's application, since most of the contaminant particles found in a sputtering chamber of a semiconductor manufacturing process are non-spherical.

[1] However, as explained later in this detailed description, particle monitor 310 can be easily modified to provide two closely spaced laser beams to detect both spherical and non-spherical particles. Such a monitor would measure the difference in intensity, when a particle passes through one of the laser beams, between the scattered and the unscattered beam. As will be appreciated by one of ordinary skill, upon consideration of the detailed description, such a particle monitor also uses the quasi-bright field approach of the present invention.

FIG. 1 shows particle monitor 310 installed for measuring the particle level of the shielded area in process chamber 300. Particle monitor 310 includes a single mode laser diode 311, such as Sony 301U which has an output power of 50 mW at 790 nm wavelength. A laser beam 351 is collimated by beam collimator 312, and passes through polarizer 313, which removes the polarization noises. Laser beam 351 then passes through a long focal length cylinder lens 314 to create a focus in the plasma 302. To modify particle monitor 310 to detect spherical particles, a beam displacer can be placed between polarizer 313 in the focal plane of cylindrical lens 314, so as to create two closely spaced parallel laser beams.

The focussed laser beam 351 emerging from cylindrical lens 314 enters the shielded area of sputtering chamber 300 through window 301 and emerges, after passing through plasma 302, from window 303. A beam splitter 316 oriented 45 degrees from the polarization direction of laser beam 351 splits the laser beam into orthogonally polarized laser beams 351a and 351b. Laser beams 351a and 351b then each impinge onto a separate photocell (not shown) within detector 315 for measuring the laser beam's intensity. The output signals of the photocells are calibrated to provide the same output signal when no scattering of laser beam 351 in the shielded area of process chamber 300 occurs. Since a particle preferentially scatters light from one of the polarizations, a difference amplifier can be used to sense a difference in the photocell currents due to the passing of the particle through the laser beam.

In particle monitor 310, the optical components are placed outside the shielded region of process chamber 300 to prevent coating by metal species sputtered. Further, windows 301 and 303 are provided to preserve the quality of the vacuum, so that particle detection can be accomplished in a non-invasive manner, without affecting the sputtering process in the shielded region of process chamber 300.

To preserve the integrity of the vacuum in process chamber 300, windows 301 and 303 are sapphire plates that are compression sealed, using small o-rings, to ports of process chamber 300. To prevent coating of windows 301 and 303, shield tubes 304 and 305 are used. Shield tubes 304 and 305 are long tubes of cross sectional dimensions slightly larger than the cross section of laser beam 351. In the present embodiment, laser beam 351 is approximately 1×3 mm when it enters process chamber 300. Accordingly, shield tubes 304 and 305 are provided to each have a cross section of 3×5 mm. Shield tubes 304 and 305 each provide an extra millimeter around the cross section of laser beam 351, so that deposition on the walls of shield tubes 304 and 305 does not block the path of laser beams 351.

Shield tubes 304 and 305 are effective in preventing deposition on windows 301 and 303 because, when compared to the mean free path ("MFP") of the metal atoms dislodged from the target, shield tubes 304 and 305 are long and narrow. The MFP is the average distance λ travelled by the atom in the vacuum before collision with another atom or particle. For a 10 millitorr vacuum, λ=0.5 cm. Thus, for such vacuum, shield tubes 304 and 305 are chosen to have a length of about 5 cm, or 10λ, to suppress deposition on windows 301 and 303, as long as each dimension of the cross section of shield tube 304 and 305 is less than λ. A long and narrow shield tube minimizes the solid angle subtended from the plasma 302 to windows 301 and 303, reducing the portion of the plasma 302's glow reaching windows 301 and 303, thereby reducing particle monitor 310's sensitivity to optical plasma noise. By (i) providing shield tubes 304 and 305, (ii) measuring the differential intensity of the emerging laser beam 351 in orthogonal directions of polarization, and/or (iii) providing a laser optical filter at the detection end of particle monitor 310, potential interference from plasma 302 is reduced. Shield tubes 304 and 305 can each be provided with a larger size cross section where it opens into the shielded region of process chamber 300, but a smaller cross section along most of the shield tube to reduce metal deposition on the optics.

Figure 2:
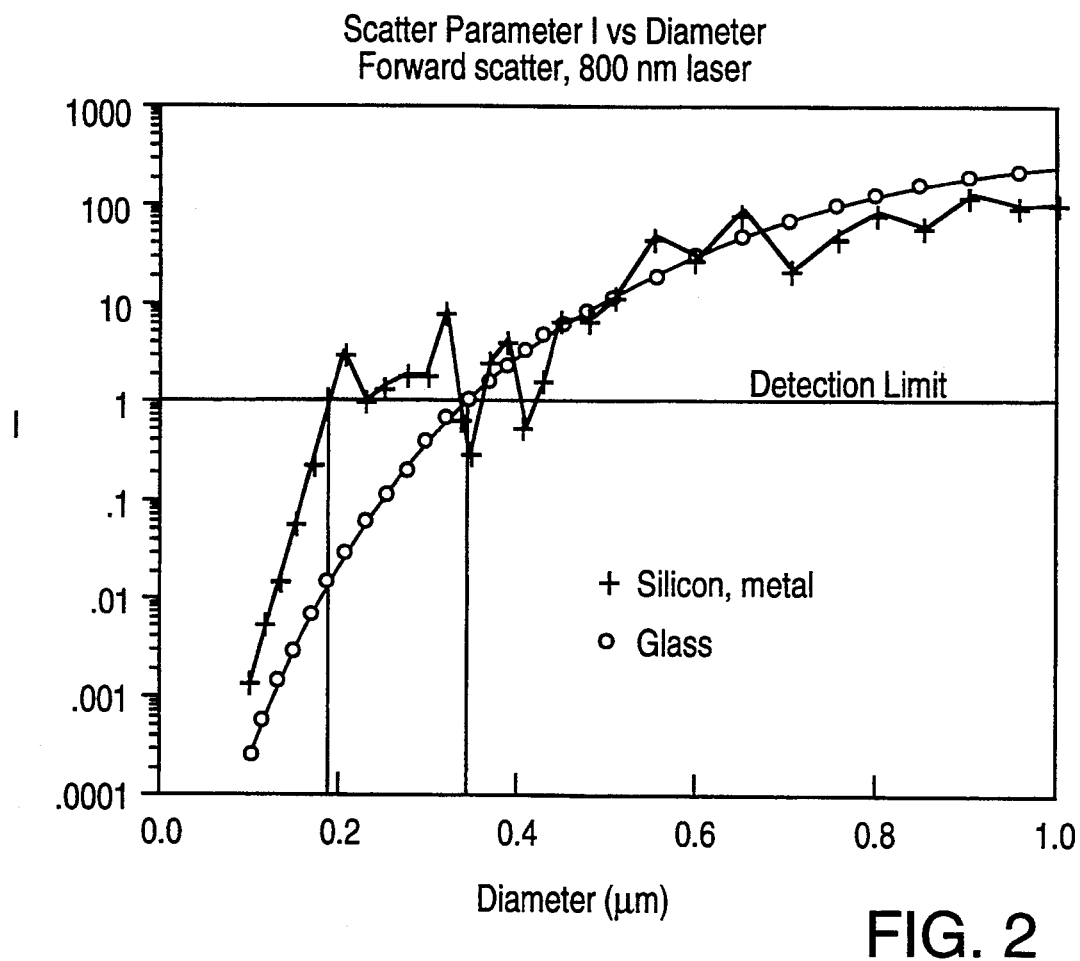
FIG. 2 graphs, for particle monitor 310, scattering parameter I against particle diameter, as calculated using Mie scattering theory for the refractive indices for silicon or metal and glass.

FIG. 2 graphs, for particle monitor 310, scattering parameter I against particle sizes, as calculated using Mie scattering theory for the refractive indices for silicon or metal and glass. As shown in FIG. 2, particle monitor 310 is able to detect silicon or metal particles greater than 0.2 microns in diameter, and glass particles of greater than 0.35 microns in diameter. In a sputtering chamber, however, glass particles are often quickly coated by the sputtered metal, so as to take on the characteristics of metal particle.

Figure 3:
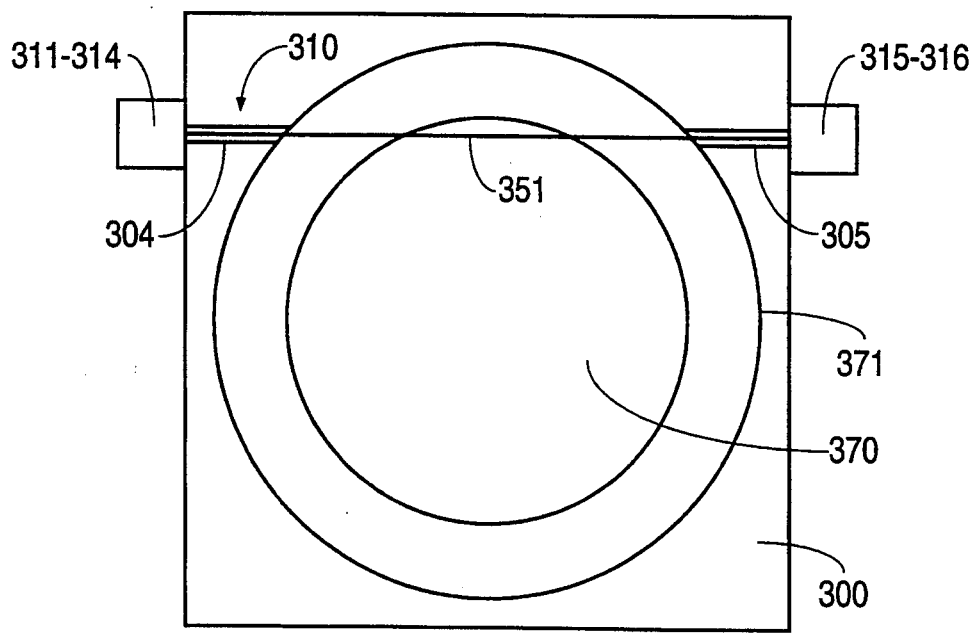
FIG. 3 is a plan view of process chamber 300, showing the placement of particle monitor 310 offset from a center portion of process chamber 300.

The present invention does not require projecting laser beam 351 directly through plasma 302. In fact, as shown in FIG. 3, which is a plan view of process chamber 300, the path of laser beam 351 can be offset from a center portion of process chamber 300. FIG. 3 also shows semiconductor wafer 370 under processing, and the shielded region 371 of process chamber 300. Such placement of particle monitor 310 is possible because the particles to be detected are charged by plasma 302. Consequently, the particles to be detected move with the internal electric and magnetic fields (the electric fields are the electric fields of plasma 302, whereas the magnetic fields are often introduced externally to make erosion of the sputtering target even). Since the present invention does not impose the path of laser beam 351, the entry and exit points of laser beam 351 into and out of the shielded region 371 of process chamber 300 can be selected based on convenience. For example, the entry and exit points of laser beam 351 can be chosen to take advantage of existing flanges as ports for respective placements of the laser source and the photodetectors, and their associated optical components. If such convenient ports do not exist, mirrors can be used to deflect laser beam 351 to a convenient region for placement of the laser source and the photodetectors.

Figure 4:
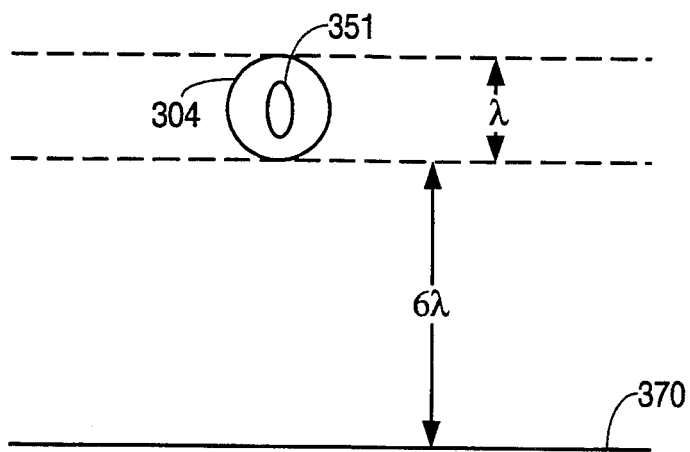
FIG. 4 shows, in accordance with the present invention, a laser beam of elliptical cross section, so as to maximize the area through which particles may pass, thereby maximizing the particle detection area of the laser beam.

To maximize the width of laser beam 351 through which particle may pass, so as to maximize the particle detection area, laser beam 351 can be provided with an elliptical cross section, with the major axis oriented perpendicular to the predominant direction of particle flow, as shown in FIG. 4. In this manner, a small laser beam, and consequently a small cross section for the shield tubes also, can be used to provide a good count rate and an acceptable probability of detecting particles in plasma 302.

The charge on a particle to be detected and, therefore, the particle's velocity as the particle is swept through laser beam 351 can be computed. The charge Q is given by $$Q = eN = \frac{\epsilon_0 rkT}{e} \ln\sqrt{\frac{M_e}{M_i}} \tag{1}$$

where e is the charge (coulombs) of an electron, N is the number of electrons on the particle, $\epsilon_0$ the permitivity of free space, r is the radius of the particle, k is Boltzman's constant, T is the electron temperature, and $m_e$ and $m_i$ are the respective masses of the electron and ions in the plasma.

Figure 5:
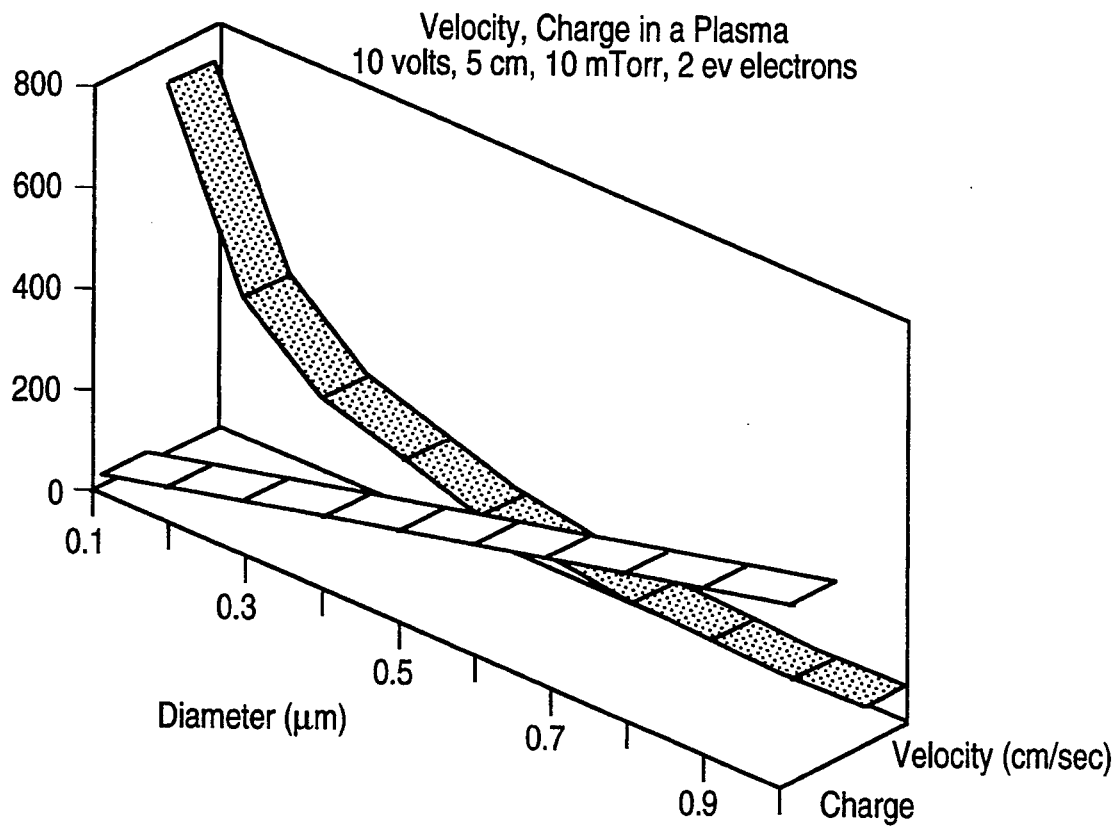
FIG. 5 shows (i) for a plasma of argon ions and electrons with a temperature corresponding to 2 eV, the charge (in number of electrons) on a particle as a function of the particle's diameter; and (ii) the estimated velocity of the particle passing through laser beam 351 as a function of the particle's diameter.

Using equation (1), the charge on a particle as a function of diameter can be computed. FIG. 5 shows, for a plasma of argon ions and electrons with a temperature corresponding to 2 eV, the charge (in number of electrons) on a particle as a function of the particle's diameter.

FIG. 5 also shows the estimated terminal velocity of the particle passing through laser beam 351 as a function of the particle's diameter. The terminal velocity of a particle passing through laser beam 351 is calculated using the equation:

$$v = Q\left(\frac{V}{X}\right)\frac{C}{3\pi n d} \quad (2)$$

where C is the Cunningham correction factor, given by:

$$C = 1 + \frac{2.52\lambda}{d} \quad (3)$$

in which d is the particle diameter, n is the viscosity of gas molecules in plasma 351, V is the voltage drop across plasma 351, and x is the length of the plasma glow. The remaining variables are as defined in equation (1).

Figure 6:
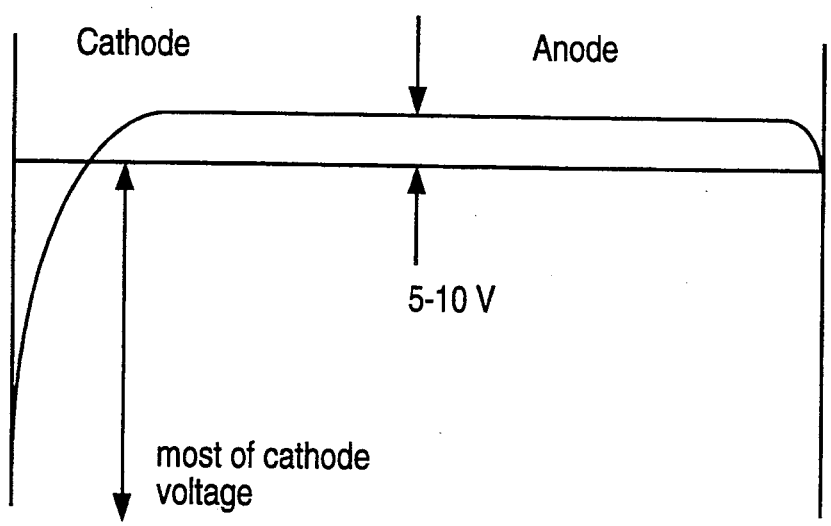
FIG. 6 shows the distribution of voltage across a plasma, as a function of the distance from the cathode.

In FIG. 5, the terminal velocity of the particle passing through laser beam 351 is estimated assuming that approximately 10 volts is dropped across a 5 cm plasma column, with the remaining of the voltage across the cathode and the semiconductor wafer dropped near the cathode, as is typical for plasmas. FIG. 6 shows a typical voltage distribution in a plasma, as a function of the distance from the cathode.

As shown in FIG. 5, the velocity of a particle passing through laser beam 351 is relatively low, in the order of a few meters per second. Thus, particle monitor 310, having a capability of detecting particles of velocities in excess of 20 m/sec, can readily be used to detect particles in a sputtering plasma.

Finally, with respect to particle monitor 310's effect on the manufacturing process, two primary considerations are (i) the effect of particle monitor 310 on metal deposition uniformity and (ii) the effect on the electric fields within process chamber 300. A change in electric field in process chamber 300 may change, for example, the erosion pattern of the sputtering target.

The effect of particle monitor 310 on metal deposition uniformity in process chamber 300 is determined by the mean free path λ. This is because deposited atoms are mainly neutral, so the holes in the shielding (i.e. the respective ends 306 and 307 of tubes 304 and 305 opposite windows 301 and 303) used to admit the laser beam can perturb the symmetry of the chamber. However, since holes 306 and 307 are several MFps from the semiconductor wafer, any perturbation due to the asymmetry of the shielded region of process chamber 300 introduced by holes 306 and 307 is smoothed by the random collisions of the deposition atoms. Consequently, the overall effect due to holes 306 and 307 is negligible. Further, the effect on electric fields due to introducing holes 306 and 307 in process chamber 300 extends only over the Debye shielding distance, given by:

$$\lambda_d = \sqrt{\frac{kT\epsilon_0}{ne^2}} \quad (4)$$

where n is the plasma density, and the other variables are those defined above with respect to equations (1)–(3).

For any typical plasma density, the Debye shielding distance is on the order of 0.01 cm, which is very small compared to the dimensions of process chamber 300. Therefore, holes 306 and 307 do not have a significant effect on the electric fields of process chamber 300.

The above detailed description is illustrative of the specific embodiments of the present invention and is not to be construed as limiting. Numerous modifications and variations within the scope of the present invention are possible. The present invention is defined by the claims following.

What is claimed is:

1. An apparatus for monitoring particles in a process chamber for a sputter deposition process using plasma, said process chamber having first and second ports allowing access to said plasma in said process chamber, comprising:

a laser source for providing an incident laser beam;

a set of optical components for collimating, polarizing and focussing said laser beam through said first and second ports on said plasma; and a detector for detecting from a measurement of the phase of said incident laser beam particles in said plasma passing through said incident laser beam.

2. An apparatus as in claim 1, further comprising:

a first shield tube attached to said first port of said process chamber, said first shield tube allowing said incident laser beam to pass into said process chamber thereby allowing said incident laser beam to pass through said plasma; and a second shield tube attached to said second port of said process chamber, said second shield tube allowing said incident laser beam, having passed through said plasma, to exit said process chamber.

3. An apparatus as in claim 1, wherein said incident laser beam having a predetermined polarization, and wherein said detector detects a phase shift in polarization in said incident laser beam of predetermined polarization.

4. An apparatus as in claim 1, wherein said set of optical components split said incident laser beam into orthogonally polarized first and second laser beams, said first and second laser beam being spaced in a predetermined distance, such that both said first and second laser beam pass into said process chamber through said first shield tube, pass through said plasma and exit from said process chamber through said second shield tube; and wherein said detector detects a difference in intensity between said first and second laser beams when a particle passes through one of said first and second laser beams.

5. An apparatus as in claim 1, wherein said laser beam has an oval cross section oriented such that the major axis of said cross section is aligned substantially perpendicular to a direction of particle flow.

6. An apparatus as in claim 2, wherein said first and second shield tubes each a length greater than three mean free paths of said particles and a width less than one mean free path of said particles.

7. An apparatus as in claim 1, wherein internal electric and magnetic fields drive particles through the laser beam.

8. An apparatus as in claim 1, wherein said detector comprises a beam splitter for splitting said incident laser beam into orthogonally polarized laser beams, said detector having photocells placed to detect the intensity of each of said orthogonally polarized laser beams.

9. An apparatus as in claim 1, wherein said incident laser beam is linearly polarized.

10. A method for detecting particles in a process chamber for a sputter deposition process using plasma, said process chamber having first and second ports allowing access to said plasma in said process chamber, comprising the steps of:

providing an incident laser beam;

providing a set of optical components for collimating, polarizing and focussing said incident laser beam, so as to allow said incident laser beam to enter said process chamber through said first port, passing through said plasma and exiting said process chamber through said second port; and providing a detector for detecting from said laser beam whether or not particles in said plasma pass through said laser beam.

11. A method as in claim 10, further comprising the steps of:

providing a first shield tube attached to said first port of said process chamber, said first shield tube allowing said laser beam to pass into said process chamber thereby allowing said laser beam to pass through said plasma;

providing a second shield tube attached to said second port of said process chamber, said second shield tube allowing said laser beam, having passed through said plasma, to exit said process chamber;

12. A method as in claim 10, wherein said step of providing an incident laser beam provides said incident laser beam in a predetermined polarization, and wherein said step of providing a detector provides a detector for detecting a phase shift in the polarization in said laser beam of predetermined polarization.

13. A method as in claim 11, where, in said step of providing a set of optical components, said optical components split said laser beam into orthogonally polarized first and second laser beams, said first and second laser beams being spaced in a predetermined distance, such that both said first and second laser beams pass into said process chamber through said first shield tube, pass through said plasma and exit from said process chamber through said second shield tube; and wherein said step of providing a detector, provides a detector for detecting a difference in intensity between said first and second laser beams when a particle passes through one of said first and second laser beams.

14. A method as in claim 10, wherein said step of providing an incident laser beam provides a laser beam of an oval cross section oriented such that the major axis of said cross section is aligned substantially perpendicular to a direction of particle flow.

15. A method as in claim 11, wherein said steps of providing first and second shield tubes each provides a shield tube of a length greater than three mean free paths of said particles and a width less than one mean free path of said particles.

16. A method as in claim 10, further comprising the step of positioning said laser beam such that internal electric and magnetic fields drive particles through the laser beam.

17. A method as in claim 10, wherein said step of providing a detector provides a beam splitter for splitting said incident laser beam into orthogonally polarized laser beams, and provides photocells placed to detect the intensity of each of said orthogonally polarized laser beams.

18. A method as in claim 10, wherein said incident laser beam is linearly polarized.

* * * * *